United States Patent
Martens et al.

(10) Patent No.: US 9,585,594 B2
(45) Date of Patent: Mar. 7, 2017

(54) METHOD OF PRODUCING PERSONALIZED RF COIL ARRAY FOR MR IMAGING GUIDED INTERVENTIONS

(75) Inventors: Hubert Cecile Francois Martens, Eindhoven (NL); Elizabeth Anne Moore, 's-Hertogenbosch (NL); Celilia Possanzini, Nijmegen (NL); Marco Hubertus Johannes Nijenhuis, Eindhoven (NL); Michel Gerardus Pardoel, Mierlo (NL); Clemens Bos, Eindhoven (NL); Aaldert Jan Elevelt, Best (NL); Daniel Wirtz, Hamburg (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 303 days.

(21) Appl. No.: 14/117,556

(22) PCT Filed: May 9, 2012

(86) PCT No.: PCT/IB2012/052309
§ 371 (c)(1),
(2), (4) Date: Nov. 13, 2013

(87) PCT Pub. No.: WO2012/156866
PCT Pub. Date: Nov. 22, 2012

(65) Prior Publication Data
US 2015/0000112 A1    Jan. 1, 2015

(30) Foreign Application Priority Data

May 16, 2011 (EP) .................................... 11166210

(51) Int. Cl.
*A61B 5/05*    (2006.01)
*G01R 33/34*    (2006.01)
(Continued)

(52) U.S. Cl.
CPC .............. *A61B 5/055* (2013.01); *A61B 34/20* (2016.02); *B29C 67/0088* (2013.01);
(Continued)

(58) Field of Classification Search
CPC .............. G01R 33/34; G01R 33/34007; G01R 33/34084; A61B 5/05; A61B 5/055;
(Continued)

(56) References Cited

U.S. PATENT DOCUMENTS 5,905,378 A    5/1999   Giaquinto
2004/0212269 A1*   10/2004   Decristofaro ............. H01F 3/02
                                                                                                                                                  310/216.065
(Continued)

FOREIGN PATENT DOCUMENTS

JP      02200243     8/1990
JP      06181907     7/1994
(Continued)

OTHER PUBLICATIONS

Artemov, Dmitri et al "Switchable Multicoil Array for MR Micro-Imaging of Breast Lesions", Magnetic Resonance in Medicine, vol. 41, 1999, pp. 569-574.
(Continued)

*Primary Examiner* — A. Dexter Tugbang

(57) ABSTRACT

A method of manufacturing a personalized radio frequency (RF) coil array for magnetic resonance (MR) imaging guided interventions includes: acquiring diagnostic image data reflecting the anatomy of a portion of a patient's body; planning an intervention on the basis of the diagnostic image data, wherein a field of the intervention within the patient's body portion is determined; and arranging one or more RF coils on a substrate which is adapted to the patient's anatomy, in such a manner that the signal-to-noise ratio of (Continued)

MR signal acquisition via the one or more RF coils from the field of the intervention is optimized.

11 Claims, 2 Drawing Sheets

(51) Int. Cl.
  *H01F 41/04* (2006.01)
  *A61B 5/055* (2006.01)
  *H01F 3/02* (2006.01)
  *B29C 67/00* (2006.01)
  *G06F 17/50* (2006.01)

(52) U.S. Cl.
  CPC . *G01R 33/34007* (2013.01); *G01R 33/34084* (2013.01); *G06F 17/50* (2013.01); *H01F 3/02* (2013.01); *H01F 41/04* (2013.01); *A61B 2034/2065* (2016.02); *A61B 2090/374* (2016.02); *Y10T 29/49018* (2015.01); *Y10T 29/49069* (2015.01); *Y10T 29/49073* (2015.01); *Y10T 29/49075* (2015.01); *Y10T 29/532* (2015.01)

(58) Field of Classification Search
  CPC ..... B29C 67/0088; G06F 17/50; G06F 19/00; Y10T 29/532; Y10T 29/49018; Y10T 29/49069; Y10T 29/49073; Y10T 29/49075; H01F 3/02; H01F 41/04
  See application file for complete search history.

(56) References Cited

U.S. PATENT DOCUMENTS

| | | | |
|---|---|---|---|
| 2005/0080333 A1 | 4/2005 | Piron | |
| 2007/0016003 A1 | 1/2007 | Piron | |
| 2007/0148633 A1* | 6/2007 | Sakezles | A61B 5/05 435/4 |
| 2008/0007250 A1 | 1/2008 | Wiggins | |
| 2008/0088309 A1* | 4/2008 | Eberler | G01R 33/34 324/318 |
| 2008/0211498 A1 | 9/2008 | Dannels | |
| 2009/0048508 A1 | 2/2009 | Gill et al. | |
| 2010/0256479 A1 | 10/2010 | Park | |
| 2010/0329414 A1* | 12/2010 | Zhu | G01R 33/34084 378/4 |
| 2011/0110572 A1 | 5/2011 | Guehring et al. | |

FOREIGN PATENT DOCUMENTS

| | | |
|---|---|---|
| JP | 2005118427 A * | 5/2005 |
| JP | 2010-094156 A1 | 4/2010 |
| JP | 2010142411 A1 | 7/2010 |
| WO | 2008078239 A1 | 7/2008 |

OTHER PUBLICATIONS

Vogan, John et al "Manipulation in MRI Devices using Electrostrictive Polymer Actuators: With an Application to Reocnfigurable Imaging Coils", Proceedings of the 2004 IEEE International Conf on Robotics and Automation, pp. 2498-2504.

Gotschal, Uli et al "Transmit-Receive Phased Array for MR Guided Spine Interventional Procedures", Proceedings of the International Society Magnetic Resonance in Medicine, vol. 10, 2002.

Kaufman, B.M. et al "Coil System for Optimal MR Mammography and MR-Guided Intervention", Proceedings of the International Society Magnetic Resonance in Medicine, vol. 17, 2009.

Liu, H. et al "MR Monitored Neurosurgical Procedures at 1.5 Tesla", Proceedings of the International Society Magnetic Resonance in Medicine, 1998.

Nnewihe, Anderson N. et al "Custom-Fitted 16-Channel Bilateral Breast Coil for Bidirectional Parallel Imaging", Magnetic Resonance in Medicine, vol. 66, 2011, pp. 281-289.

Keil, B. et al "Age-Optimized 32-Channel Brain Arrays for 3T Pediatric Imaging", Proceedings of the International Society Magnetic Resonance in Medicine, 2010.

Keil, B. et al "A 64-Channel Array Coil for 3T Head/Neck/C-Spine Imaging", Proceedings of the International Society Magnetic Resonance in Medicine, 2011.

* cited by examiner

METHOD OF PRODUCING PERSONALIZED RF COIL ARRAY FOR MR IMAGING GUIDED INTERVENTIONS

CROSS-REFERENCE TO PRIOR APPLICATIONS

This application is the U.S. National Phase application under 35 U.S.C. §371 of International Application No. PCT/IB2012/052309, filed on May 9, 2012, which claims the benefit of European Patent Application No. 11166210.2, filed on May 16, 2011. These applications are hereby incorporated by reference herein.

FIELD OF THE INVENTION

The invention relates to the field of magnetic resonance (MR) imaging. It concerns a method of manufacturing a personalized RF coil array for MR imaging guided interventions. Moreover, the invention relates to a computer program and to a computer workstation.

Image-forming MR methods which utilize the interaction between magnetic fields and nuclear spins in order to form two-dimensional or three-dimensional images are widely used nowadays, notably in the field of medical diagnostics, because for the imaging of soft tissue they are superior to other imaging methods in many respects, do not require ionizing radiation and are usually not invasive.

BACKGROUND OF THE INVENTION

According to the MR method in general, the body of the patient to be examined is arranged in a strong, uniform magnetic field whose direction at the same time defines an axis (normally the z-axis) of the co-ordinate system on which the measurement is based. The magnetic field produces different energy levels for the individual nuclear spins in dependence on the magnetic field strength which can be excited (spin resonance) by application of an electromagnetic alternating field (RF field) of defined frequency (so-called Larmor frequency, or MR frequency). From a macroscopic point of view, the distribution of the individual nuclear spins produces an overall magnetization which can be deflected out of the state of equilibrium by application of an electromagnetic pulse of appropriate frequency (RF pulse) while the magnetic field of the RF pulse extends perpendicular to the z-axis, so that the magnetization performs a precession about the z-axis. This motion of the magnetization describes a surface of a cone whose angle of aperture is referred to as flip angle. The magnitude of the flip angle is dependent on the strength and the duration of the applied electromagnetic pulse. In the case of a so-called 90° pulse, the spins are deflected from the z axis to the transverse plane (flip angle 90°). The RF pulse is radiated toward the body of the patient via a RF coil arrangement of the MR device. The RF coil arrangement typically surrounds the examination volume in which the body of the patient is placed.

After termination of the RF pulse, the magnetization relaxes back to the original state of equilibrium, in which the magnetization in the z direction is built up again with a first time constant $T_1$ (spin lattice or longitudinal relaxation time), and the magnetization in the direction perpendicular to the z direction relaxes with a second time constant $T_2$ (spin-spin or transverse relaxation time). The variation of the magnetization can be detected by means of receiving RF coils which are arranged and oriented within the examination volume of the MR device in such a manner that the variation of the magnetization is measured in the direction perpendicular to the z-axis. The decay of the transverse magnetization is accompanied, after application of, for example, a 90° pulse, by a transition of the nuclear spins (induced by local magnetic field inhomogeneities) from an ordered state with the same phase to a state in which all phase angles are uniformly distributed (dephasing). The dephasing can be compensated by means of a refocusing pulse (for example a 180° pulse). This produces an echo signal (spin echo) in the receiving coils.

In order to realize spatial resolution in the body, linear magnetic field gradients extending along the three main axes are superposed on the uniform magnetic field, leading to a linear spatial dependency of the spin resonance frequency. The signal picked up in the receiving coils then contains components of different frequencies which can be associated with different locations in the body. The signal data obtained via the receiving coils corresponds to the spatial frequency domain and is called k-space data. The k-space data usually includes multiple lines acquired with different phase encoding. Each line is digitized by collecting a number of samples. A set of k-space data is converted to a MR image by means of Fourier transformation or other suitable algorithms.

The lack of harmful effects on the examined patient and the operator make MR imaging well-suited for "interventional radiology", wherein the acquired and reconstructed MR images are used to guide invasive procedures. The general goal of imaged guidance is to apply imaged-based information to the processes of diagnosis and therapy. Known MR imaging-guided therapy systems use pre-operatively acquired MR images to create anatomic models, which provide localization, targeting, and visualization of the 3D anatomy. These models support pre-operative planning to define and optimize access strategies and to simulate planned interventions. These models connect image coordinates with the actual position defined by an instrument's location in the surgical field. Thus, they enable a surgeon to navigate and execute procedures with full knowledge of the surrounding anatomy.

In a plurality of practical applications, shifts and deformations of soft tissues occur during surgery because of mechanical factors, physiological motion, swelling, or hemorrhage. These changes may displace organs or their tissue components to such a degree that pre-operatively acquired MR imaging-based 3D models cannot be registered with the patient's actual anatomy. In this situation the ultimate solution for accurate MR imaging-guided surgery is real-time intra-operative MR imaging or at least frequent updating of the volumetric MR images during interventional procedures. This results in methods that can continuously detect changes of the position of various tissue components and locate the targets of the interventions and their environments in order to define trajectories to the lesion to be treated. Hence, the justification of intra-operative MR imaging is the change in anatomy during surgeries or the change of tissue integrity during therapy. The goal is to allow MR imaging-guided therapy to make full use of the anatomic and functional information accessible by current MR imaging methods. By providing the physician with current MR image information, safety and efficiency of surgical or interventional procedures is significantly improved.

A problem is that it is difficult in a surgical setting to optimally place the RF coils required for MR signal acquisition around the respective body portion in such a fashion that (i) a good signal-to-noise ratio (SNR) is obtained and (ii) a good access to the interventional field is assured for the physician.

SUMMARY OF THE INVENTION

From the foregoing it is readily appreciated that there is a need for an improved RF coil arrangement for MR imaging guided interventions that enables high-quality intra-operative MR imaging as well as good access to the patient.

In accordance with the invention, a method of manufacturing a personalized RF coil array for MR imaging guided interventions is disclosed. The method comprises the steps of:

acquiring diagnostic image data reflecting the anatomy of a portion of a patient's body;

planning an intervention on the basis of the diagnostic image data, wherein an interventional field within the patient's body portion is determined;

arranging one or more RF antennae on a substrate, which is adapted to the patient's anatomy, in such a manner that the signal-to-noise ratio of MR signal acquisition via the one or more RF antennae from the interventional field is optimized.

The invention proposes a personalized design of a RF coil array for MR imaging-guided surgical procedures. The design of the RF coil array, i.e. the sizes, shapes, and/or positions of the RF antennae, is based on the anatomy of the portion of the patient's body to be treated and on the surgery plan. The diagnostic image data, which may comprise X-ray images, CT images, and/or MR images, is acquired pre-operatively in a first step. Anatomic models may be created on the basis of this diagnostic image data, which enable localization, targeting, and visualization of the 3D anatomy of the patient's body portion. In a second step, pre-operative planning is performed on the basis of the acquired diagnostic image data in order to define the interventional field and to optimize the access strategies. Finally, the design of the RF coil array is derived from the results of the surgery planning. The sizes, shapes and/or positions of one or more RF antennae on the substrate is automatically computed, thereby optimizing the signal-to-noise ratio of the MR signals acquired intra-operatively from the interventional field.

The substrate, on which the one or more RF antennae are arranged, is adapted to the shape of the patient's body, so that the RF coil array can be placed firmly, in close proximity, and in a well-defined position on the patient's body during the surgical invention. Preferably, both the shape of the substrate and the position of the substrate on the patient's body are derived from the previously acquired diagnostic image data and from the planning results.

According to a preferred embodiment of the invention, an access path to the interventional field is further determined during the step of planning the intervention, wherein the one or more RF antennae are arranged on the substrate in such a manner that the signal-to-noise ratio of MR signal acquisition from the interventional field and from the access path is optimized. In this embodiment, the optimization criteria determining the design of the RF coil array are extended so as to ensure the acquisition of high-quality MR images not only from the interventional field itself, i.e. the target region of the intervention, but also from the access path, which the surgeon takes to reach the lesion to be treated. Acquisition of high-quality MR images throughout the complete intervention is thus achieved.

According to a further preferred embodiment of the invention, one or more apertures are provided on the substrate in such a manner that the access path is kept clear when the substrate is attached to the patient's body. The size, the shape, and the locations of apertures in the substrate, via which the surgeon accesses the patient's body portion, are derived from the pre-operatively acquired diagnostic image data and from the results of the surgery plan according to this embodiment of the invention. Preferably, the RF antennae are arranged on the substrate at a pre-determined minimum distance from the interventional field and/or from the access path. This ensures that the interventional field is freely accessible for the surgeon. Furthermore, interferences between the RF antennae and the surgical instruments are avoided.

According to yet another preferred embodiment of the invention, the sizes and/or the shapes of the RF antennae and/or their positions on the substrate are computed on the basis of a simulation of the RF electromagnetic field distribution during MR signal acquisition. This means that a RF electromagnetic field simulation is performed in order to automatically determine the optimum sizes, shapes, and/or positions of the RF antennae in order to optimize the signal-to-noise ratio for MR signals acquired from the interventional field and/or from the access path. As explained above, this optimization may be constrained by the provision of one or more apertures on the substrate, which have to be kept clear from the RF antennae in order to enable access to the patient's body during surgery.

In yet another preferred embodiment of the invention, the final design of the personalized RF coil array is transferred to a rapid prototyping facility, where the personalized RF coil array is fabricated. After the fabrication step the RF coil array is ready to be used for the planned surgical intervention.

The method of the invention may further comprise the step of arranging electronic components for RF signal transmission and/or reception via the RF antennae on the substrate. Such electronic components may be, for example, RF connectors for connecting RF cables to the individual antennae, RF tuning and/or matching networks, or RF pre-amplifiers directly connected to the RF antennae. Also these electronic components may be fabricated (at least in part) by means of rapid prototyping. Per se known techniques for generating printed circuit boards and associated components by means of rapid prototyping can be used for this purpose. Further discrete electronic components, which cannot be manufactured by rapid prototyping methods, can be assembled and integrated into the personalized RF coil array in a separate manufacturing step.

In a possible embodiment of the invention, the RF antennae, which are arranged on the substrate of the personalized RF coil array, are standardized RF coil modules. The use of standardized and pre-fabricated RF coil modules in the personalized RF coil array of the invention facilitates the manufacturing process. The individual standardized RF coil modules are positioned on the substrate and/or interconnected such that the signal-to-noise ratio for MR signals acquired from the interventional field and/or from the access path is optimized.

The invention does not only relate to a method, but also to a computer program, which comprises instructions for:

loading diagnostic image data reflecting the anatomy of a portion of a patient's body;

interactive planning of an intervention on the basis of the loaded diagnostic image data, wherein an interventional field within the patient's body portion is determined;

computing sizes, shapes and/or positions of one or more RF antennae to be arranged on a substrate, which is adapted to the patient's anatomy, in such a manner that the signal-to-noise ratio of MR signal acquisition via the one or more RF antennae from the interventional field is optimized.

Such a computer program can be loaded into a dedicated computer workstation comprising a display unit, via which interactive surgery planning on the basis of the loaded diagnostic image data is enabled. The computer workstation can be directly connected to a rapid prototyping facility, which manufactures a personalized RF coil array comprising the substrate and the RF antennae arranged on the substrate according to the automatically computed sizes, shapes, and/or positions.

BRIEF DESCRIPTION OF THE DRAWINGS

The enclosed drawings disclose preferred embodiments of the present invention. It should be understood, however, that the drawings are designed for the purpose of illustration only and not as a definition of the limits of the invention. In the drawings.

DETAILED DESCRIPTION OF EMBODIMENTS

Figure 1:
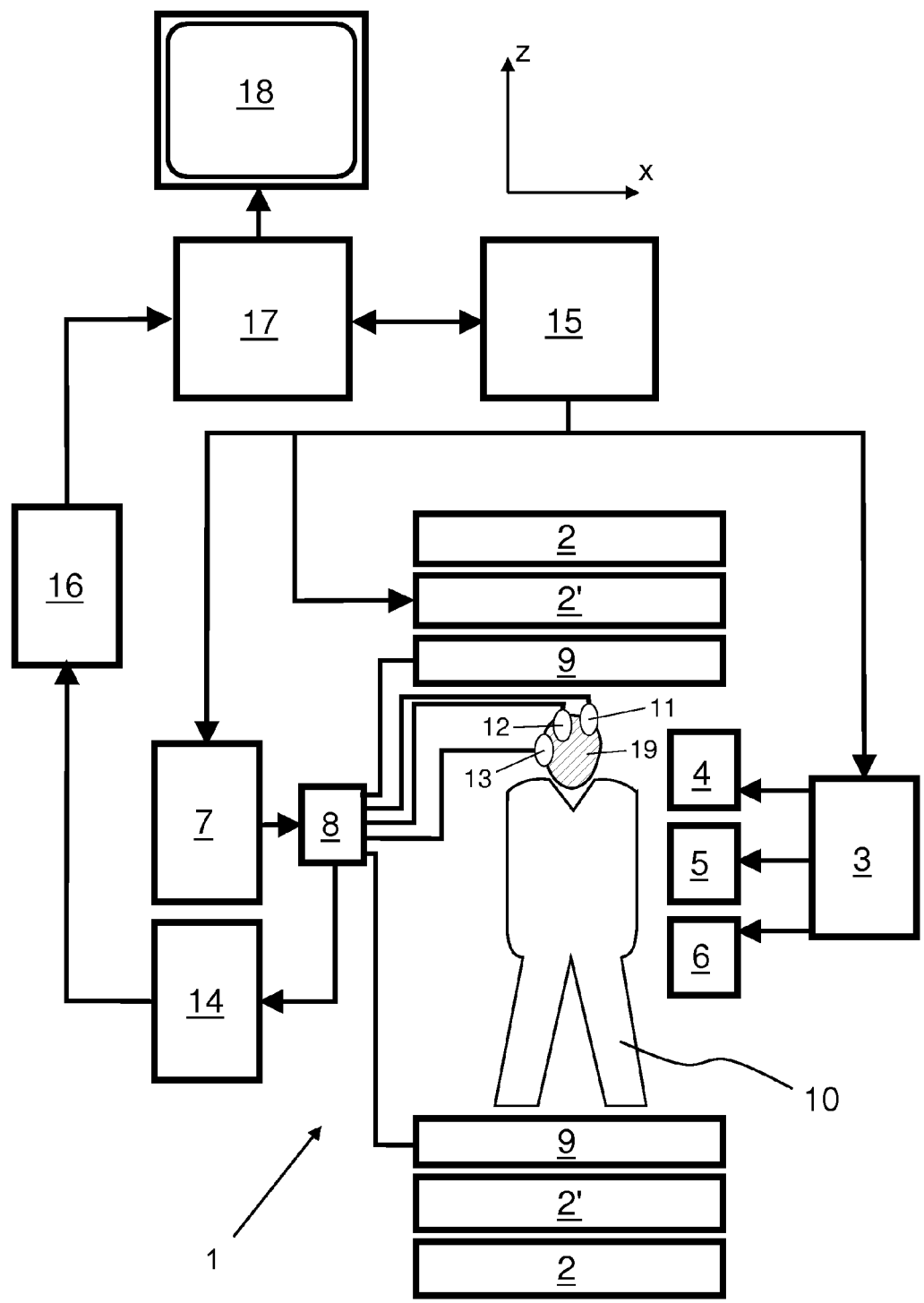
FIG. 1 schematically shows a MR device including a personalized RF coil array according to the invention.

With reference to FIG. 1, a MR device 1 is shown. The device comprises superconducting or resistive main magnet coils 2 such that a substantially uniform, temporally constant main magnetic field $B_0$ is created along a z-axis through an examination volume. The device further comprises a set of ($1^{st}$, $2^{nd}$, and—where applicable—$3^{rd}$ order) shimming coils 2', wherein the current flow through the individual shimming coils of the set 2' is controllable for the purpose of minimizing $B_0$ deviations within the examination volume.

A magnetic resonance generation and manipulation system applies a series of RF pulses and switched magnetic field gradients to invert or excite nuclear magnetic spins, induce magnetic resonance, refocus magnetic resonance, manipulate magnetic resonance, spatially and otherwise encode the magnetic resonance, saturate spins, and the like to perform MR imaging.

Most specifically, a gradient pulse amplifier 3 applies current pulses to selected ones of whole-body gradient coils 4, 5 and 6 along x, y and z-axes of the examination volume. A digital RF frequency transmitter 7 transmits RF pulses or pulse packets, via a send-/receive switch 8, to a -body RF coil 9 to transmit RF pulses into the examination volume. A typical MR imaging sequence is composed of a packet of RF pulse segments of short duration which taken together with each other and any applied magnetic field gradients achieve a selected manipulation of nuclear magnetic resonance. The RF pulses are used to saturate, excite resonance, invert magnetization, refocus resonance, or manipulate resonance and select a portion of a body 10 positioned in the examination volume. The MR signals are also picked up by the body RF coil 9.

For intra-operative generation of MR images of the head region of the body 10, for example by means of parallel imaging, a set of local array RF antennae (coils) 11, 12, 13 are placed on a mask 19, which constitutes a substrate adapted to the patient's head anatomy within the meaning of the invention. The RF coils 11, 12, 13 are positioned contiguous to the head region selected for imaging. Hence, high-quality MR images can be acquired, for example, during brain surgery. The array coils 11, 12, 13 can be used to receive MR signals induced by body-coil RF transmissions.

The resultant MR signals are picked up by the body RF coil 9 and/or by the array RF coils 11, 12, 13 and demodulated by a receiver 14, preferably including a pre-amplifier (not shown). The receiver 14 is connected to the RF coils 9, 11, 12 and 13 via send-/receive switch 8.

A host computer 15 controls the current flow through the shimming coils 2' as well as the gradient pulse amplifier 3 and the transmitter 7 to generate any of a plurality of MR imaging sequences, such as echo planar imaging (EPI), echo volume imaging, gradient and spin echo imaging, fast spin echo imaging, and the like. For the selected sequence, the receiver 14 receives a single or a plurality of MR data lines in rapid succession following each RF excitation pulse. A data acquisition system 16 performs analog-to-digital conversion of the received signals and converts each MR data line to a digital format suitable for further processing. In modern MR devices the data acquisition system 16 is a separate computer which is specialized in acquisition of raw image data.

Ultimately, the digital raw image data is reconstructed into an image representation by a reconstruction processor 17 which applies a Fourier transform or other appropriate reconstruction algorithms, such like SENSE or GRAPPA. The MR image may represent a planar slice through the patient, an array of parallel planar slices, a three-dimensional volume, or the like. The image is then stored in an image memory where it may be accessed for converting slices, projections, or other portions of the image representation into appropriate format for visualization, for example via a video monitor 18 which provides a human-readable display of the resultant MR image.

Figure 2:
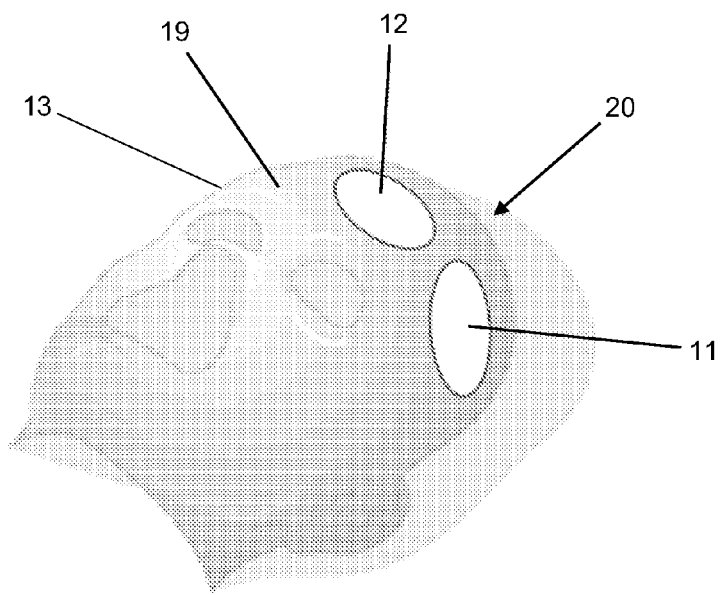
FIG. 2 shows the RF coil array of FIG. 1 in more detail.

FIG. 2 shows the personalized RF coil array of the invention in more detail. As can be seen in FIG. 2, the substrate 19 is a mask (fabricated, for example, from a suitable plastic material) which is adapted to the shape of the patient's head. The mask 19 comprises apertures for the patient's eyes, mouth and nose. RF coils 11, 12, 13 are arranged on the mask 19 in such a manner that the signal-to-noise ratio of MR signals acquired via the RF coils 11, 12, 13 from an interventional field within the patient's brain is optimized. The personalized RF coil array shown in FIG. 2 further comprises an aperture at the planned site for craniotomy to allow the surgeon to access the skull and brain. The corresponding access path is indicated by arrow 20 in FIG. 2. The personalized RF coil array is designed and manufactured in an automated fashion by means of rapid prototyping. Therein, the sizes, shapes, and positions of the RF coils 11, 12, and 13 are computed by means of simulation of electromagnetic field distributions in order to optimize the signal-to-noise ratio taking into account the interventional field and access path resulting from the planning of the intervention. The necessary apertures of the mask 19 are used as constraints in the optimization procedure.

Figure 3:
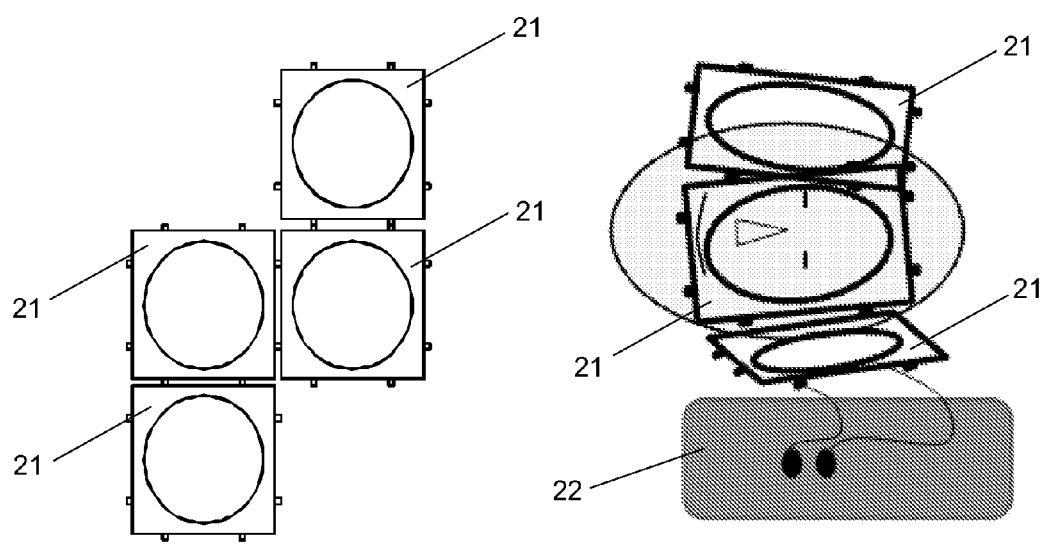
FIG. 3 shows another embodiment of the personalized RF coil array according to the invention.

FIG. 3 illustrates an embodiment of the invention, in which standardized and interconnectible RF coil modules are used. The coil modules 21 are arranged on the mask 19 in accordance with the above-described optimization criteria. The interconnected RF coil modules 21 are connected via cable connections to a RF unit 22 comprising, for example, a RF pre-amplifier.

The invention claimed is:
1. A method of producing a personalized array of one or more radio frequency (RF) coils for a magnetic resonance

(MR) imaging guided surgical procedure on a portion of a patient's body, the method comprising:

creating a model of anatomy of the portion of a patient's body using acquired image data from at least one of X-ray, computed tomography (CT), and MR diagnostic images of the portion of a patient's body;

determining, based on the acquired image data, an interventional area within the portion of the patient's body and an access path to the interventional area, the access path limiting access strategies during the surgical procedure; and providing an arrangement of a substrate by disposing the array of one or more RF coils on the substrate wherein;

sizes, shapes and positions of the one or more RF coils are computed based on the acquired image data for optimal signal-to-noise ratio of an MR signal acquired from the determined access path and the interventional area, and;

a shape of the substrate is adapted to a shape of the portion of the patient's body based on the acquired image data so as to position the array of RF coils firmly in close proximity on the portion of the patient's body during the surgical procedure.

2. The method of claim 1, further comprising providing the substrate with one or more apertures to keep the access path clear when the substrate is attached to the patient's body during the surgical procedure.

3. The method of claim 1, wherein the RF coils are arranged on the substrate at a pre-determined minimum distance from the interventional area.

4. The method of claim 1, wherein at least one of the sizes, shapes, and positions on the substrate of the one or more RF coils on the substrate are computed based on a simulation of the RF electromagnetic field distribution during MR signal acquisition.

5. The method of claim 1 further comprising using rapid prototyping for forming the array of one or more RF coils.

6. The method of claim 1, further comprising arranging on the substrate electronic components for at least one of RF signal transmission and RF signal reception via the RF coils.

7. The method of claim 1, wherein the array of RF coils include one or more standardized RF coil modules.

8. The method of claim 1, wherein providing the arrangement of the substrate and the array of one or more RF coils disposed on the substrate includes providing a mask with the array of one or more RF coils disposed on the mask.

9. The method of claim 8, wherein providing the mask includes providing apertures therein for the patient's eyes, nose and mouth.

10. The method of claim 8, further comprising providing the mask with at least one aperture for providing surgical access to the patient's skull and brain.

11. The method of claim 1, wherein the RF coils are arranged on the substrate at a pre-determined minimum distance from the access path.

* * * * *